United States Patent
Else et al.

(10) Patent No.: US 10,433,563 B2
(45) Date of Patent: Oct. 8, 2019

(54) USE OF AN ANTI-STALING ENZYME MIXTURE IN THE PREPARATION OF BAKED BREAD

(75) Inventors: Anthony James Else, Gorinchem (NL); Kari Margrete Tronsmo, Bingen am Rhein (DE); Ludger-Andreas Niemann, Bingen am Rhein (DE); Johannes Hubertus Elise Moonen, Utrecht (NL)

(73) Assignee: CORBION GROUP NETHERLANDS B.V., Amsterdam (NL)

(*) Notice: Subject to any disclaimer, the term of this patent is extended or adjusted under 35 U.S.C. 154(b) by 846 days.

(21) Appl. No.: 13/593,317

(22) Filed: Aug. 23, 2012

(65) Prior Publication Data

US 2013/0059031 A1    Mar. 7, 2013

(30) Foreign Application Priority Data

Aug. 25, 2011 (EP) ..................... 11178839

(51) Int. Cl.
| | |
|---|---|
| *A21D 8/04* | (2006.01) |
| *A21D 13/00* | (2017.01) |
| *A21D 10/00* | (2006.01) |

(52) U.S. Cl.
CPC .......... *A21D 8/042* (2013.01); *A21D 10/002* (2013.01); *C12Y 302/01001* (2013.01); *C12Y 302/01003* (2013.01)

(58) Field of Classification Search
CPC .. A21D 8/042; A23V 2002/00; C12N 9/2417; C12N 9/2414; C12N 9/2425; A23L 1/034; C12Y 301/01004; Y02E 50/17; C12P 19/14
USPC .............. 426/7, 20, 549; 536/23.2; 435/202
See application file for complete search history.

(56) References Cited

U.S. PATENT DOCUMENTS

| | | | |
|---|---|---|---|
| 5,023,094 A | 6/1991 | Van Eijk | |
| 5,589,207 A | 12/1996 | Larsen et al. | |
| 6,197,352 B1 * | 3/2001 | Olesen | ........................... 426/20 |
| 2010/0021587 A1 | 1/2010 | Chang et al. | |

FOREIGN PATENT DOCUMENTS

| | | |
|---|---|---|
| EP | 0 154 135 A2 | 9/1985 |
| WO | WO-91/04669 A1 | 4/1991 |
| WO | WO-2011/039324 A1 | 4/2011 |

OTHER PUBLICATIONS

Christophersen, C., et al., "Enzymatic Characterisation of Novamyl, a Therapeutic alpha-Amylase", Starch, vol. 50, No. 1, 1998, pp. 39-45.
Extended European Search Report for EP 11178839.4—dated Mar. 2, 2012.
Gerrard J A et al: "The role of maltodextrins in the staling of bread", Journal of Cereal Science 1997 Grain Foods Res. Unit, New Zealand Institute for Crop & Food Research Ltd., Private Bag 4704, Christchurch, New Zealand LNKD-DOI:10.1006/JCRS.1997.0121, vol. 26, 1997, pp. 201-209, XP002669573.
Hug-Iten S et al: "Staling of bread: role of amylose and amylopectin and influence of starch-degrading enzymes", Cereal Chemistry, American Association of Cereal Chemists. Minneapolis, US, vol. 80, No. 6, Jan. 1, 2003 (Jan. 1, 2003), pp. 654-661, XP009156489.

* cited by examiner

*Primary Examiner* — Hamid R Badr
(74) *Attorney, Agent, or Firm* — Gilberto M. Villacorts; Sunit Talapatra; Foley & Lardner LLP

(57) ABSTRACT

The invention provides a process of preparing baked bread by baking a farinaceous dough, said process comprising incorporating into the dough a combination of two or more enzymes including:

maltogenic amylase in an amount of 750-75,000 maltogenic amylase units (MAU) per kg of flour, said maltogenic amylase having an optimum temperature above 50° C.;

amyloglucosidase in an amount of 0.01-3.0 amyloglucosidase units (AGU) per unit of MAU activity The combination of maltogenic amylase and amyloglucoside is a very effective anti-staling agent.

15 Claims, No Drawings

USE OF AN ANTI-STALING ENZYME MIXTURE IN THE PREPARATION OF BAKED BREAD

TECHNICAL FIELD OF THE INVENTION

The present invention relates to the prevention of staling of baked bread. More particularly, the present invention relates to the use of an enzyme mixture to prevent such staling, said enzyme mixture comprising maltogenic amylase and amyloglucosidase.

BACKGROUND OF THE INVENTION

Staling of baked foodstuffs (such as bread) is a well-known problem. Staling, or "going stale", is a chemical and physical process in baked foods that reduces their palatability. Staling becomes evident as an increase of the firmness of the crumb, a decrease of the elasticity or resilience of the crumb, and changes in the crust, which becomes tough and leathery. The increase in crumb firmness, which is considered as the most important aspect of staling, is recognized by the consumer a long time before the bread product has otherwise become unsuitable for consumption.

Staling is not, as is commonly believed, simply a drying-out process due to evaporation of water. Bread will stale even in a moist environment and stales most rapidly at temperatures just above freezing. Although the precise mechanism of staling is still unknown, one important mechanism appears to be migration of moisture from the starch granules into the interstitial spaces, and realigning of amylose and amylopectin molecules of starch. The process of the realignment of the starch molecules is called retrogradation. On retrogradation, crystal-like structures may form that are similar to those originally present in the starch granules, and the process is referred to as recrystalisation. Retrogradation normally results in stale bread with a harder, less resilient crumb texture.

Starch is an essential constituent of baked foodstuffs. During the baking process, the starch becomes gelatinized and absorbs large amounts of water; meanwhile the protein denatures. Immediately after baking, the starch begins to retrograde. The firmness of the crumb increases, although this is still regarded as an advantage in the first hours. In particular the sliceability and chewing characteristics of the crumb improve during this period.

It is assumed that the unbranched starch fraction, amylose, retrogrades first, followed by the branched fraction of the starch, amylopectin, during further storage. At the same time the crumb becomes stiffer, and in the course of time increasingly less elastic and eventually dry and hard: the bread has become stale. In addition, the crust looses crispness and becomes leathery during storage. It is assumed that this is a result of water being released by retrogradation and diffusing outward from the crumb to the crust.

It is undisputed that the causal key reaction for all of these staling phenomena is starch retrogradation. Suppressing or circumventing this phenomenon is the subject matter of numerous protective rights and publications.

One strategy for hindering, at least partly, the considerable firming of the crumb during storage has already been long known: the crumb is made softer from the beginning. The means of choice to do this are emulsifiers such as mono/diglycerides, which are added to the dough and produce a crumb structure that is particularly soft from the beginning. The use of α-amylase derived from fungi such as *Aspergillus oryzae* has a similar effect. It acts upon damaged starch particles, thereby lowering the viscosity of the dough and producing fermentable sugars. As a consequence, the finished baked article has larger volume, which is consistent with softer crumb. Aside from the fact that the fresh bread is soft, this strategy does not prevent or inadequately prevents the development of a harder, less elastic consistency of the crumb when it becomes stale.

A further strategy is to reduce retrogradation by enzyme-mediated partial hydrolysis of the two starch fractions during baking. Enzyme-mediated hydrolysis of the crumb should preferably take place after the starch has been gelatinized, i.e., above about 65° C. As a consequence the structure of the starch in the baked product is radically altered, limiting its ability to retrograde. The fragments produced by partial hydrolysis of the starch are too short to be able to recrystallize and associate with the remaining high molecular weight starch, thereby reducing speed of recrystallization. A heat-stable maltogenic amylase from *Bacillus* is commercially available under the trade name Novamyl 10,000® (product of Novozymes A/S, Denmark) and is widely used in the baking industry as an anti-staling agent due to its ability to reduce retrogradation by hydrolyzing starch at starch gelatinization temperature (WO 91/04669). Novamyl 10,000® is most active at 60-70° C. (Christophersen, C., et al., 1997, Starch, vol. 50, No. 1, 3945).

Since significant costs are associated with the use of maltogenic amylase as an anti-staling agent in baked bread, there is a need for a more cost-effective anti-staling agent.

SUMMARY OF THE INVENTION

The inventors have been able to provide an enzymatic anti-staling agent for baked bread that is extremely effective and that has a lower cost-in-use than existing enzymatic anti-staling agents, notably thermostable maltogenic amylases.

The inventors have discovered that the effectiveness of thermostable maltogenic amylases as anti-staling agents can be improved substantially by combining such amylases with amyloglucosidase.

Accordingly, one aspect of the invention relates to process of preparing a baked bread by baking a farinaceous dough, said process comprising incorporating into the dough a combination of two or more enzymes including:

maltogenic amylase in an amount of 750-75,000 maltogenic amylase units (MAU) per kg of flour, said maltogenic amylase having an optimum temperature above 50° C.;

amyloglucosidase in an amount of 0.01-3.00 amyloglucosidase units (AGU) per unit of MAU activity.

Another aspect of the invention relates to a baked bread that is obtained by the aforementioned process.

The combined use of maltogenic amylase and amyloglucosidase is described WO 2011/039324. This international patent application describes a method for preparing a steamed bread composition, comprising the step of making a dough used to prepare steamed bread with one or more maltogenic alpha-amylases, one or more raw starch degrading enzymes, and at least one lipolytic enzyme. Examples 7-10 of WO 2011/039324 describe the preparation of steamed breading using a combination of Opticake™ 50 BG (maltogenic alpha-amylase) and Trametes™ AMG (raw starch degrading enzyme).

In addition, Gerrard et al. (*The Role of Maltodextrins in the Staling of Bread*, Journal of Cereal Science 26 (1997) 201-209) describe the results of a study into the effect of added alpha-amylase (Novamyl®) and/or very high levels of added glucoamylase (GA300N, Genencor) on staling of bread were investigated.

The use of a combination of a heat-stable amyloglucosidase and a non-heat stable amylase in a frozen, leavened laminated dough is described in U.S. Pat. No. 5,589,207. More specifically, this U.S. patent teaches to employ a fungal amylase which becomes inactive at temperature 60° C. in combination with an amyloglucosidase which remains active above 60° C. The examples of the patent describe the combined use of the fungal amylase Fungamyl® MG 35000 and the amyloglucosidase AMG 300 MG. In the U.S. patent it is explained that the use of the heat-stable amyloglucosidase ensures formation of monosaccharides after yeast activity has ceased to be available so that these monosaccharides can participate in crust colouring reactions.

DETAILED DESCRIPTION OF THE INVENTION

The invention provides a process of preparing baked bready by baking a farinaceous dough, said process comprising incorporating into the dough a combination of two or more enzymes including:
  maltogenic amylase in an amount of 750-75,000 maltogenic amylase units (MAU) per kg of flour, said maltogenic amylase having an optimum temperature above 50° C.;
  amyloglucosidase in an amount of 0.01-3.0 amyloglucosidase units (AGU) per unit of MAU activity.

The term "maltogenic amylase" as used herein refers to a starch degrading enzyme having IUPAC Classification number EC 3.2.1.1. (glucan 1,4-α-maltohydrolase) that is capable of hydrolyzing maltotriose to maltose and glucose.

The term "amyloglucosidase" as used herein refers to another starch degrading enzyme having IUPAC Classification number EC 3.2.1.3. Amyloglucosidase (or 1,4-α-D-glucan glucohydrolase) not only cleaves the last α(1-4) glycosidic linkages at the non-reducing end of amylose and amylopectin, yielding glucose, but also cleaves α(1-6) glycosidic linkages.

Whenever reference is made herein to the "optimum temperature" of an enzyme what is meant is the temperature at which the enzyme activity is highest. For the maltogenic amylase the optimum temperature is suitably determined at pH 5.0. For the amyloglucosidase the optimum temperature is suitably determined at pH 4.2.

The "optimum pH" of an enzyme is the pH at which the enzyme activity is highest. The optimum pH is suitably measured at 60° C.

One unit of maltogenic amylase activity (MAU) is defined as the amount of enzyme required to release one nanomol of maltose per second at a concentration of 10 mg of maltotriose substrate per ml of 0.1 M citrate buffer, pH 5.0 at 37° C.

One unit of amyloglucosidase activity (AGU) is defined as the amount of enzyme required to release one nanomol of glucose per second at a concentration of 10 mg of maltose substrate per ml of 0.1 M citrate buffer, pH 5.0 at 37° C.

The present method can suitably employ different types of amyloglucosidases. Preferably, the amyloglucosidase employed is a polypeptide that is encoded by a DNA sequence that is found in a fungal strain of *Aspergillus, Rhizopus* or *Talaromyces*. Examples of suitable fungi include *Aspergillus niger, Rhizopus delemar, Rhizopus niveus, Rhizopus oryzae* and *Talaromyces emersonii*. Most preferably, the amyloglucosidase employed in accordance with the present invention is a polypeptide that is encoded by a DNA sequence that is found in a strain of *Aspergillus niger*.

The amyloglucosidase employed in the present process typically has an optimum pH in the range of L5-5.5, especially in the range of 2.0-4.5.

The amyloglucosidase is advantageously incorporated in the dough in an amount of 40-40,000 AGU per kg of flour, more preferably of 80-23,000 AGU per kg of flour. Expressed differently, the amyloglucosidase is preferably incorporated in the dough in an amount of 0.05-0.50 AGU per unit of MAU activity, most preferably in an amount of 0.10-0.30 AGU per unit of MAU activity.

The maltogenic amylase employed in the present process preferably has an optimum temperature in the range of 52-90° C., most preferably in the range of 55-85° C.

The optimum pH of the maltogenic amylase preferably lies in the range of 4.0-7.5, most preferably in the range of 4.5-7.0.

The inventors have found that staling can be minimized very effectively even if the amyloglucosidase has an optimum temperature that is substantially lower than the optimum temperature of the maltogenic amylase. Preferably, the optimum temperature of the amyloglucosidase is at least 10° C., more preferably at least 12° C. and most preferably at least 14° C. lower than the optimum temperature of the maltogenic amylase. Typically, the optimum temperature of the amyloglucosidase is less than 55° C.

The maltogenic amylase employed in accordance with the present invention preferably is a polypeptide that is encoded by a DNA sequence that is found in a *Bacillus* strain, most preferably in a strain of *Geobacillus. stearothermophilus*.

The maltogenic amylase is typically incorporated in the dough in an amount of 1,000-40,000 MAU per kg of flour, most preferably of 1,500-7,500 MAU per kg of flour.

In accordance with one preferred embodiment, the bread dough employed in the present process is a mixed rye/wheat flour dough. In accordance with another preferred embodiment, the bread dough is wheat flour dough.

In the present process the farinaceous dough is typically prepared by combining flour, water, yeast, the maltogenic amylase, the amyloglucosidase and optionally other bakery ingredients.

Besides the maltogenic amylase and the amyloglucosidase, the present process may employ other food-grade enzymes, such as α-amylase, xylanase and protease.

The farinaceous dough is preferably baked at a temperature in excess of 180° C., more preferably at a temperature in excess of 200° C. In case the dough is a yeast containing dough, the dough is preferably fermented prior to baking.

In accordance with a particularly preferred embodiment of the present process the dough is prepared by incorporating a bread improver into the dough, said bread improver comprising a combination of two or more enzymes including:
  maltogenic amylase in an amount of 7,500-75,000,000 maltogenic amylase units (MAU) per kg of dry matter, said maltogenic amylase having an optimum temperature above 50° C.;
  amyloglucosidase in an amount of 0.01-3.0 amyloglucosidase units (AGU) per unit of MAU activity.

The aforementioned bread improver is typically employed in the bread dough in a concentration of 0.1-10%, especially of 0.3-5% by weight of flour.

Typically, the amyloglucosidase is present in the bread improver in an amount of 100-120,000,000 AGU per kg of dry matter, even more preferably in an amount of 500-30, 000,000 AGU per kg of dry matter and most preferably of 750-4,000,000 AGU per kg of dry matter.

Besides the maltogenic amylase and the amyloglucosidase the bread improver employed in the present process preferably comprises one or more, more preferably two or more and most preferably three or more of the following bakery ingredients:
emulsifier;
triglyceride oil or fat;
other enzymes, notably enzymes selected from α-amylases, hemicellulases, lipases, proteases and combinations thereof;
gluten;
ascorbic acid;
preservation aids, for example, calcium propionate;
chemical leavening agent;
cereal flour.

Typically, the aforementioned bakery ingredients together represent at least 50 wt. %, more preferably at least 70 wt. % of the bread improver.

The bread improver used in the present process preferably is a liquid or a particulate product. More preferably, the bread improver is a powder or a granulate having a mass weighted average particle size in the range of 10-1000 μm, more preferably of 50-800 μm, most preferably of 100-500 μm.

Another aspect of the invention relates to a baked bread that is obtained by a process as defined herein before.

The invention is further illustrated by, but not limited to the following examples.

EXAMPLES

Example 1

Rye/wheat bread dough was prepared on the basis of the recipe shown in Table 1 and by mixing the ingredients in a Diosna mixer for 6 min slow, and 2 min fast.

TABLE 1

|  | % by weight of flour |
| --- | --- |
| Rye flour Type 1150 | 70 |
| Wheat flour Type 550 | 30 |
| Water | 80 |
| Bread improver [1] | 2.5 |
| Acid improver [2] | 2.5 |
| Salt | 2.1 |
| Compressed yeast | 1.5 |
| Anti-staling enzyme | 0.008 (80 ppm) |

[1] WB 24 from CSM Deutschland GmbH
[2] Backsauer R22 from CSM Deutschland GmbH

Two different doughs were prepared using the following the anti-staling enzymes:
Product I: 80 ppm Novamyl® 10,000 BG: 6,080 MAU per kg flour
Product II: 60 ppm Novamyl® 10,000 BG: 4,560 MAU per kg flour+20 ppm Bakezyme® AG 800 BG: 840 AGU per kg flour (ex DSM, Netherlands)

The activities of the aforementioned commercial enzyme preparations are specified in Table 2

TABLE 2

|  | Enzyme activity |
| --- | --- |
| Novamyl ® 10,000 BG | 76,000 MAU/g |
| Bakezyme ® AG 800 BG | 42,000 AGU/g |

After mixing the dough was rested for 30 min at ambient. After that 1100 g pieces of dough were moulded, put into a tin, and fermented for 50 min at 32° C. After fermentation the dough pieces were baked for 50 min in a deck oven. The oven temperature was programmed to remain at 260° C. for 10 minutes and then to decrease linearly from 260 to 230° C. during the following 40 min.

Breads were stored in a standard polyethylene bag at ambient up to 9 days.

Crumb firmness was measured by a TA.XT Plus texture analyzer from Stable Micro Systems. The method used was as follows: A cylinder of bread crumb was cut from the centre of the baked bread. The diameter of the cylinder was 45 mm and the length was 30 mm. The diameter of the measuring probe was 50 mm, test speed was 2 mm/sec, and the probe entered the breadcrumb for 10 mm. The force required to do this was measured in g and equals hardness.

The results obtained for the two different products, based on 4 replicates, are shown in Table 3.

TABLE 3

|  | Crumb hardness (in g) | |
| --- | --- | --- |
| Storage time | Product I | Product II |
| 3 days | 1574 | 1578 |
| 4 days | 1817 | 1590 |
| 7 days | 1905 | 1692 |
| 8 days | 1985 | 1780 |
| 9 days | 2075 | 1914 |

Example 2

Wheat dough was prepared on the basis of the recipe shown in Table 4 and by mixing the ingredients in a Diosna spiral mixer for 2 min slow, and 6 min fast.

TABLE 4

|  | % by weight of flour |
| --- | --- |
| Wheat flour Type 550 | 100 |
| Water | 58 |
| Compressed yeast | 3.0 |
| Bakery margarine | 3.0 |
| Salt | 2.0 |
| Acid improver [1] | 1.0 |
| Calcium propionate | 0.15 |
| Anti-staling enzyme | 0.005 (50 ppm) |

[1] Backsauer R22 from CSM Deutschland GmbH

Two different doughs were prepared using the following the anti-staling enzymes:
Product I: 50 ppm Novamyl® 10,000 BG
Product II: 36 ppm Novamyl® 10,000 BG+7 ppm Bakezyme® AG 800 BG (ex DSM, Netherlands)

After mixing, the dough was rested for 10 minutes. After that 550 g pieces of dough were moulded, put into a tin, and fermented for 50 min at 32° C. Next, the dough pieces were baked for 33 min in a Wachtel deck oven at 240° C.

Breads were stored in a standard polyethylene bag at ambient up to 9 days.

Crumb firmness was measured with the same method as described in Example 1.

The results obtained for the two different products, based on 4 replicates, are shown in Table 5.

TABLE 5

| Storage time | Crumb hardness (in g) | |
| --- | --- | --- |
| | Product I | Product II |
| 3 days | 625 | 495 |
| 4 days | 682 | 574 |
| 7 days | 756 | 705 |
| 8 days | 823 | 773 |
| 9 days | 957 | 856 |

Example 3

The activity of Spezyme GA 300 N (Genencor) was determined around 1994. The measured activity was 460 AGU/µl.

Gerrard et al. (*The Role of Maltodextrins in the Staling of Bread*, Journal of Cereal Science 26 (1997) 201-209) describe an experiment in which maltogenic amylase (Novamyl®) and glucoamylase (GA300N, Genencor) were added to a bread dough in a concentration of 0.8 mg per g flour and 20 µl per g flour, respectively. Since the maltogenic amylase has an activity of 11.4 MAU per mg, it can be calculated that in this particular experiment amyloglucosidase was applied in an amount that is much higher than 3 AGU per unit of MAU activity.

The invention claimed is:

1. A process of preparing baked bread, comprising:
    (a) incorporating into farinaceous dough a combination of two or more enzymes comprising:
        (i) maltogenic amylase in an amount of 750-75,000 maltogenic amylase units (MAU) per kg of flour, said maltogenic amylase having an optimum temperature above 50° C.; and
        (ii) amyloglucosidase in an amount of 0.01-3.0 amyloglucosidase units (AGU) per unit of MAU activity; and,
    (b) baking the dough.

2. The process according to claim 1, wherein the amyloglucosidase is a polypeptide that is encoded by a DNA sequence that is found in a fungus strain of *Aspergillus niger*.

3. The process according to claim 1, wherein the amyloglucosidase has an optimum pH in the range of 1.5-5.5.

4. The process according to claim 3, wherein the amyloglucosidase has an optimum pH in the range of 2.0-4.5.

5. The process according to claim 1, wherein the amyloglucosidase is incorporated in the dough in an amount of 40-40,000 AGU per kg of flour.

6. The process according to claim 1, wherein the amyloglucosidase is incorporated in the dough in an amount of 0.05-0.50 AGU per unit of MAU activity.

7. The process according to claim 1, wherein the optimum temperature of the amyloglucosidase is at least 10° C. lower than the optimum temperature of the maltogenic amylase.

8. The process according to claim 1, wherein the maltogenic amylase has an optimum temperature in the range of 55-90° C.

9. The process according to claim 1, wherein the maltogenic amylase is a polypeptide that is encoded by a DNA sequence that is found in a strain of *Geobacillus stearothermophilus*.

10. The process according to claim 1, wherein the dough is a mixed rye/wheat flour dough.

11. The process according to claim 1, wherein the dough is prepared by combining flour, water, yeast, the maltogenic amylase, the amyloglucosidase and optionally other bakery ingredients.

12. The process according to claim 11, wherein the dough is fermented prior to baking.

13. The process according to claim 1, wherein the farinaceous dough is baked at a temperature in excess of 180° C.

14. The process according to claim 1, preparing the dough by incorporating a bread improver into the dough, said bread improver comprising a combination of two or more enzymes comprising:
    (a) maltogenic amylase in an amount of 7,500-75,000,000 maltogenic amylase units (MAU) per kg of dry matter, said maltogenic amylase having an optimum temperature above 50° C.; and
    (b) amyloglucosidase in an amount of 0.01-3.0 amyloglucosidase units (AGU) per unit of MAU activity.

15. The process according to claim 14, wherein the bread improver is a powder or a granulate having a mass weighted average particle size in the range of 10-1000 µm.

* * * * *

UNITED STATES PATENT AND TRADEMARK OFFICE
CERTIFICATE OF CORRECTION

PATENT NO. : 10,433,563 B2
APPLICATION NO. : 13/593317
DATED : October 8, 2019
INVENTOR(S) : Anthony James Else et al.

It is certified that error appears in the above-identified patent and that said Letters Patent is hereby corrected as shown below:

On the Title Page

Item (73):
Replace "CORBION GROUP NETHERLANDS B.V., Amsterdam (NL)" with -- CARAVAN INGREDIENTS INC., Lenexa, KS (US) --

Signed and Sealed this
Sixteenth Day of June, 2020

Andrei Iancu
*Director of the United States Patent and Trademark Office*